United States Patent [19]

Ratcliffe et al.

[11] 4,233,131

[45] Nov. 11, 1980

[54] PROCESS FOR PREPARING ALKYLENE EPISULFIDES AND EPISELENIDES

[75] Inventors: Charles T. Ratcliffe; James T. Yardley, both of Morristown, N.J.

[73] Assignee: Allied Chemical Corporation, Morris Township, Morris County, N.J.

[21] Appl. No.: 89,649

[22] Filed: Oct. 29, 1979

[51] Int. Cl.³ ............................................ C07D 32/000
[52] U.S. Cl. .................... 204/162 R; 260/239 R; 549/1; 549/90; 204/158 R
[58] Field of Search ................. 260/239 R; 549/1, 90; 204/158 R, 162 R

[56] References Cited

U.S. PATENT DOCUMENTS

| | | | |
|---|---|---|---|
| 2,237,096 | 4/1941 | Dearborn | 549/1 |
| 3,616,374 | 10/1971 | Goshorn et al. | 204/162 R |
| 3,616,375 | 10/1971 | Inoue | 204/162 R |
| 4,029,558 | 6/1977 | Marling | 204/158 R |
| 4,029,559 | 6/1967 | Marling | 204/158 R |

*Primary Examiner*—John D. Randolph
*Attorney, Agent, or Firm*—James Riesenfeld

[57] ABSTRACT

A process for the preparation of alkylene episulfides or episelenides is provided which comprises contacting elemental sulfur or elemental selenium, respectively, with an olefin, preferably ethylene, while irradiating with electromagnetic radiation in the infrared to ultraviolet range. The alkylene episulfides and episelenides are useful in the production of a variety of functional polymers.

10 Claims, 2 Drawing Figures

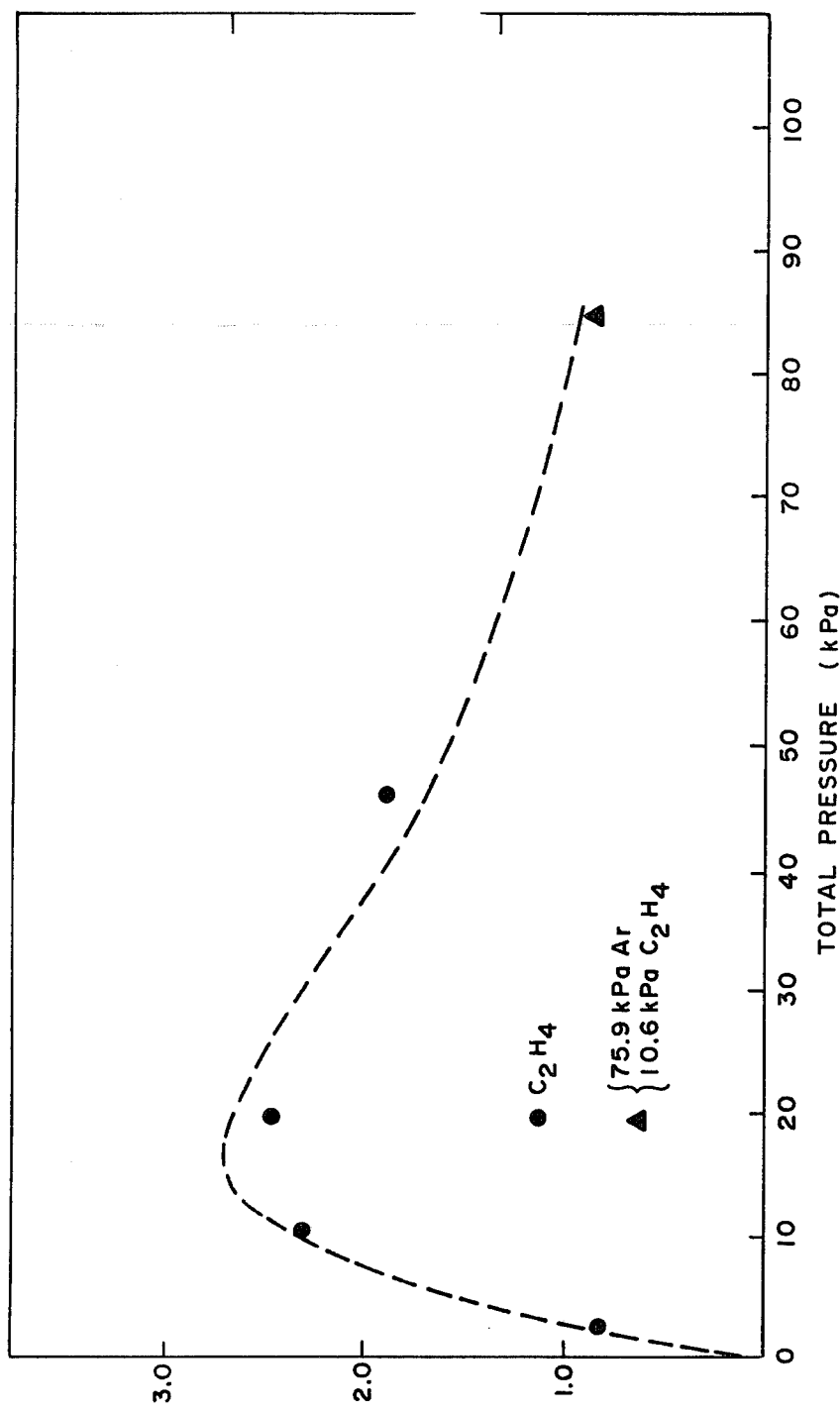

PROCESS FOR PREPARING ALKYLENE EPISULFIDES AND EPISELENIDES

DESCRIPTION

BACKGROUND OF THE INVENTION

1. Field of the Invention

This invention relates to a process for preparing alkylene episulfides or episelenides by contacting elemental sulfur or elemental selenium, respectively, with an olefin while irradiating the materials with electromagnetic radiation.

2. Description of the Prior Art

Ethylene and propylene episulfides represent highly reactive and potentially valuable monomers, useful in the production of a variety of functional polymers. Sulfur-containing polymers are most noted for their elastic properties at low temperatures, good weathering ability and resistance to ozone. Thiol terminated liquid polymers have the advantageous capability of in situ curing at room temperature, which has led to applications in sealants and adhesives. Since a large part of the total molecular weight of ethylene episulfide and propylene episulfide is sulfur, these materials could provide a low cost raw material base. Direct routes to ethylene and propylene episulfide from sulfur and the olefins, however, are not available.

The gas phase reaction of ground state S atoms with olefins to form cyclic episulfides has been extensively studied through ultraviolet photolysis of COS and $CS_2$ (H. E. Gunning and O. P. Strausz, Advances Photochem., 4, 143 (1966)). In the case of ethylene, the reaction has a low ($\sim 1.6$ kcal/mol) activation energy and proceeds with a bimolecular rate constant of $5 \times 10^{13}$ $cm^3$ molecule$^{-1}$ sec$^{-1}$ (collision probability $\sim 2 \times 10^{-3}$) at 20° C.

Current methods of ethylene episulfide preparation require the reaction of ethylene oxide with $CS_2$ or COS, the photolysis of COS in the presence of ethylene, or the reaction of ethylene oxide with an aqueous alcoholic solution of a thiocyanate. Major applications of sulfur monomers in large volume polymers have not developed due to the high synthetic cost of the monomers.

In general, the direct interaction of sulfur with olefins results in the formation of a mixture of complex polysulfides. A contributing factor to this complex mixture is the fact that sulfur exists at moderate temperatures in the highly stable $S_8$ and $S_6$ polymer forms. Temperatures of at least 600° C. are necessary to form $S_2$, a moderately reactive form of sulfur, but at these higher temperatures sulfur readily dehydrogenates potential organic reactants. Single S atoms require even higher temperatures ($\gtrsim 1700°$ C.), at which episulfides are unstable.

Only one instance has been reported in which an episulfide was formed by direct reaction of elemental sulfur with an olefin at ambient temperature (F. R. Sharp and T. L. Peppards (Chem. Ind. (1977) 664)). In that case, episulfides of some unsaturated sesquiterpene hydrocarbons (e.g., caryophyllene) were synthesized by the slow reaction of the hydrocarbon with elemental sulfur in daylight. The reaction did not proceed in the dark. The sesquiterpene hydrocarbons contain unusual olefinic linkages with chemical properties different from simple alkenes.

SUMMARY OF THE INVENTION

In accordance with the present invention, alkylene episulfides or episelenides are prepared by a process which comprises contacting elemental sulfur or elemental selenium, respectively, with an olefin while irradiating the sulfur/selenium-olefin materials with electromagnetic radiation in the infrared to ultraviolet range. The olefin has 2 to 6 carbon atoms and is represented by the formula:

$$R^1R^2C = CR^3R^4$$

wherein $R^1$, $R^2$, $R^3$ and $R^4$ are independently selected from the group consisting of hydrogen and alkyl groups of 1 to 4 carbon atoms. Suitable olefins include ethylene, propylene and any of the hexenes.

Compared with prior art processes for episulfide production, the process of this invention has several advantages. The process can be carried out at ambient temperature and is quite efficient, with photon efficiencies of ethylene episulfide production measured as high as 4%. The process avoids the production of mercaptans, which generally result from photolysis which produces $^1S$ and $^1D$ sulfur atoms. Finally, the process makes direct use of sulfur, which is readily available and relatively inexpensive.

BRIEF DESCRIPTION OF THE DRAWINGS

FIG. 2 is a graph of net ethylene episulfide yield as a function of pressure in the same embodiment of the invention.

DETAILED DESCRIPTION OF THE INVENTION

Figure 1:
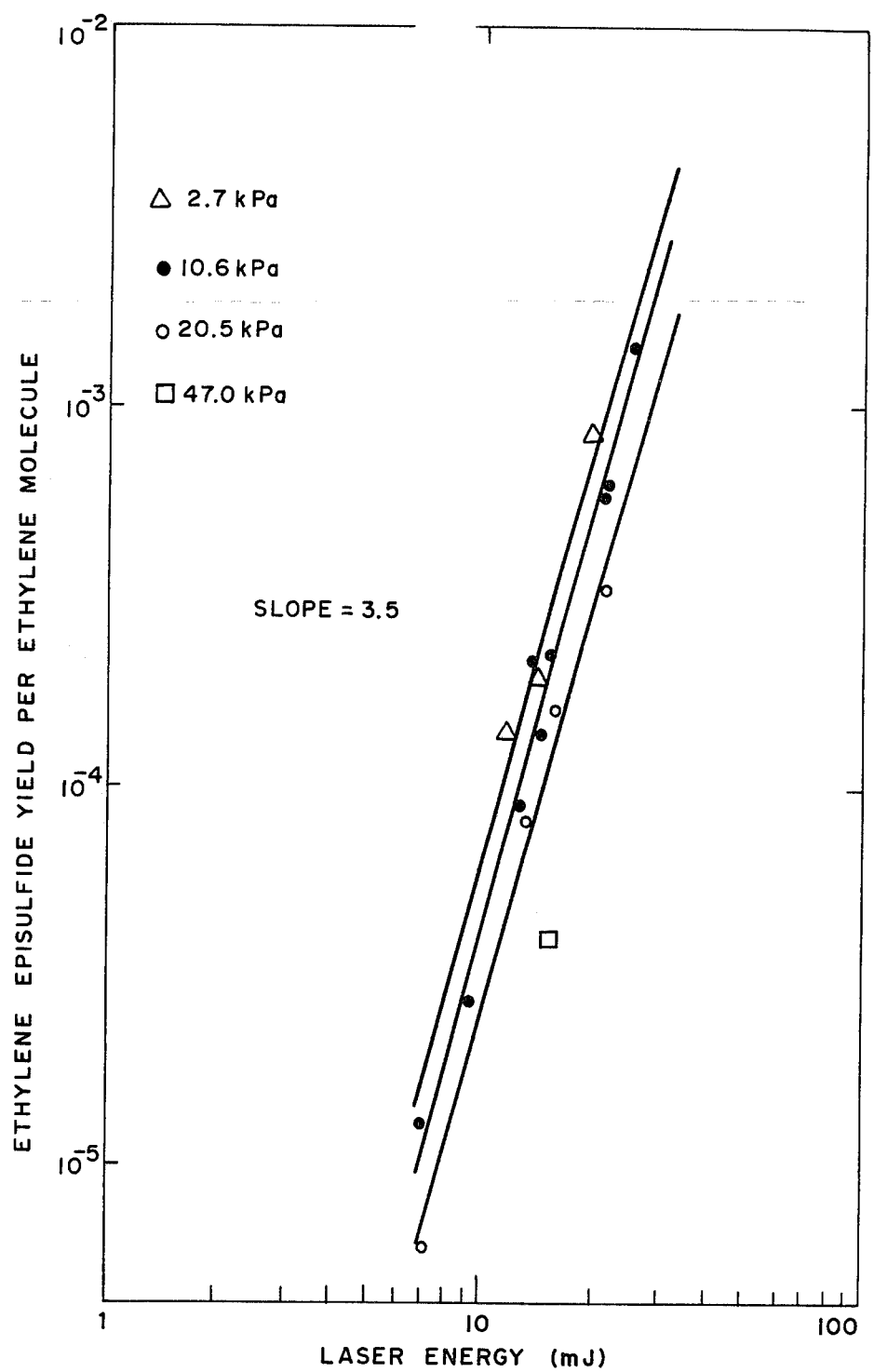
FIG. 1 is a graph of ethylene episulfide yield per ethylene molecule as a function of irradiation energy in one embodiment of the invention.

Although the process of this invention is suitable for the production of both alkylene episulfides and episelenides, the preferred embodiment is directed to alkylene episulfide production. Thus, the discussion below is directed principally to the production of episulfides, particularly ethylene episulfide, which is most preferred.

Efficiencies up to 4% are achieved in a preferred embodiment of the present process, which comprises contacting ethylene with elemental sulfur while irradiating the materials with a KrF laser. For convenience, the process is preferably performed at ambient temperature, but lower and higher temperatures may be used, limited by the stability of the materials. Sulfur reactivity at high temperatures indicates that temperatures below about 600° C. are preferred for episulfide production.

A log-log plot of ethylene episulfide yield per ethylene molecule as a function of laser energy is shown in FIG. 1 for four different ethylene pressures. The data fit a series of straight lines of slope 3.5, with increasing laser energy producing increasing yield per ethylene molecule. Although we do not wish to be bound by any theory, these data indicate that product formation occurs as a result of a nonlinear optical process involving the simultaneous or sequential absorption of at least three or four photons. The similarity of intensity dependence for several pressures indicates that the excitation mechanism is independent of ethylene pressure in the pressure region studied.

Data are plotted in FIG. 2 for excitation with 500 pulses from an unfocused KrF laser, 15.5 mJ per pulse. Ethylene pressures ranged up to 47 kPa, and a total pressure of 86.5 kPa was achieved by adding 75.9 kPa of argon to 10.6 kPa of ethylene. The data show that at low ethylene pressure the net episulfide yield is proportional to pressure. For pressures above 27 kPa the yield falls off as $p^{-2}$. Optimum operating pressure for this embodiment is about 18 kPa. Thus, ethylene pressure for ethylene episulfide preparation by the process of this invention is preferably less than about 80 kPa and more preferably between about 5 kPa and 40 kPa.

In an alternative embodiment of the present invention, elemental sulfur is irradiated with infrared to ultraviolet light in the presence of propylene to form propylene episulfide.

EXAMPLE 1

A disc of rhombic sulfur was placed at the bottom of a 200 cm$^3$ cell containing ethylene at a pressure of 20 kPa. The sample was irradiated at room temperature with a Tachisto model TAC II KrF laser, which provided ultraviolet light at 249 nm in a pulse of 12 nsec duration and 0.5 nm band width. The unfocused beam irradiated an area 12 mm×3mm on the sulfur surface. After 500 laser pulses at an energy of 20 mJ per pulse, GC analysis of the resultant gas mixture detected approximately 6.9 Pa (0.034%) of ethylene episulfide.

EXAMPLE 2

Using the procedure and apparatus of Example 1 with propylene at a pressure of 20 kPa substituted for ethylene, propylene episulfide is formed at a rate of about 4 product molecules per 100 incident photons.

We claim:

1. A process for the preparation of alkylene episulfides or episelenides which comprises contacting elemental sulfur or elemental selenium, respectively, with an olefin while irradiating the sulfur/seleniumolefin materials with electromagnetic radiation in the infrared to ultraviolet range, said olefin having 2 to 6 carbon atoms and being represented by the formula:

$$R^1R^2C=CR^3R^4$$

wherein $R^1$, $R^2$, $R^3$ and $R^4$ are independently selected from the group consisting of hydrogen and alkyl groups of 1 to 4 carbon atoms.

2. The process of claim 1 wherein elemental sulfur is irradiated.

3. The process of claim 1 wherein the olefin is ethylene.

4. The process of claim 1 wherein the olefin is propylene.

5. The process of claim 1 wherein the source of electromagnetic radiation is a laser.

6. The process of claim 1 wherein the source of electromagnetic radiation is a KrF laser.

7. The process of claim 3 wherein the ethylene pressure is less than about 80 kPa.

8. The process of claim 7 wherein the ethylene pressure is between about 5 kPa and 40 kPa.

9. The process of claim 1 wherein the process is carried out at ambient temperature.

10. The process of claim 2 wherein the process is carried out at a temperature below about 600° C.

* * * * *